United States Patent [19]

Elliott et al.

[11] Patent Number: 4,515,808

[45] Date of Patent: May 7, 1985

[54] PESTICIDES

[75] Inventors: Michael Elliott, Stevenage; Norman F. Janes, Luton; Bhupinder P. S. Khambay, Harrow Weald, all of England

[73] Assignee: National Research Development Corporation, London, England

[21] Appl. No.: 517,441

[22] Filed: Jul. 26, 1983

[30] Foreign Application Priority Data

Jul. 26, 1982 [GB] United Kingdom ............... 8221501

[51] Int. Cl.³ ..................... A01N 53/00; C07C 121/78
[52] U.S. Cl. ................. 514/521; 260/465 D; 260/465 E; 560/8; 560/55; 560/57; 560/101; 560/105; 560/118; 560/124; 564/256; 514/531; 514/534
[58] Field of Search ............ 260/465 D, 465 E; 560/8, 124, 55, 57, 101, 105, 118; 424/304, 305, 308

[56] References Cited

U.S. PATENT DOCUMENTS 3,236,889  2/1966  Pawlowski .............. 260/566
3,922,269 11/1975  Elliott et al. ............ 260/347.4

FOREIGN PATENT DOCUMENTS 0021520 1/1981 European Pat. Off. .
0067792 6/1982 European Pat. Off. .
1540474 8/1968 France .
2211454 7/1974 France .

Primary Examiner—Dolph H. Torrence
Attorney, Agent, or Firm—Oblon, Fisher, Spivak, McClelland & Maier

[57] ABSTRACT

Pesticidal compounds have the formula:

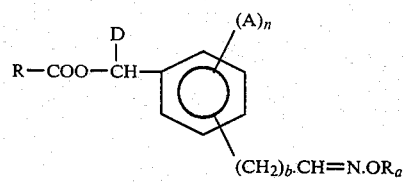

wherein D represents hydrogen or a cyano group or an ethynyl group
$R_a$ represents alkyl
A represents an alkyl group or a halogeno or trifluoromethyl group
n is 0 or an integer of 1-4, b is 0 or 1 and

RCOO is the residue of an acid RCOOH whose α-cyano-3-phenoxybenzyl ester has pesticidal properties. They are prepared by esterification methods.

22 Claims, No Drawings

PESTICIDES

BACKGROUND OF THE INVENTION

Field of the Invention

This invention relates to pesticides and in particular to pesticidal compounds, the preparation of such compounds, intermediates for use in their preparation, compositions containing such compounds and the use of such compounds and compositions to control pests, for example pests present in soil.

SUMMARY OF THE INVENTION

Accordingly the present invention comprises a compound of formula I

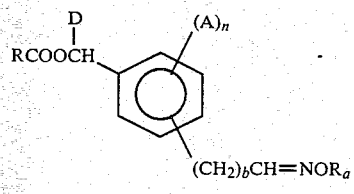

in which formula:

D represents hydrogen or a cyano group or an ethynyl group;

A represents an alkyl group (typically a $C_1$–$C_6$ alkyl group), or a halogeno group e.g. F, Cl or Br or a $CF_3$ group;

n is 0 to 4;

$R_a$ represents an alkyl group (typically a $C_1$–$C_6$ alkyl group);

b is 0 or 1.

RCOO represents a residue of an acid $RCO_2H$, whose α-cyano-3-phenoxybenzyl ester has pesticidal properties.

DESCRIPTION OF THE PREFERRED EMBODIMENTS

Although the acid residue RCOO may derive from a wide variety of acids as hereinafter described, it is preferred that the acid residue is of a cyclopropane carboxylic acid such as chrysanthemic acid or a 2,2-dimethyl-3-(dihalovinyl)cyclopropane carboxylic acid, the 2,2-dimethyl-3-(dibromovinyl)cyclopropane carboxylic acid, especially when in the (IR,cis) form being of especial interest.

Although $R_a$ typically represents a $C_1$–$C_6$ alkyl group, $C_1$–$C_4$ alkyl groups are generally preferred, especially methyl and ethyl. Activity of the compound I generally varies between the Z and E configuration in the oximino group, the E compounds usually being preferred. It is generally preferred for the substituent —$(CH_2)_b$CH=$NOR_a$ to be disposed at the 3- or 4-position in the aromatic ring with respect to the ester linkage, 3-substitution being preferred especially when D represents a cyano group.

The group A, when present, typically represents methyl, and compounds in which two alkyl, e.g. methyl, groups are disposed at the 2,6 position in the ring with respect to the ester link are of especial interest.

Compounds I of particular interest include the following esters of (IR)-cis-3-(2,2-dibromovinyl)-2,2-dimethylcyclopropane carboxylic acid:-3-methoxyiminomethylbenzyl (I; b=0, $R_a$=$CH_3$, D=H, n=0, α-cyano-3 methoxyiminomethylbenzyl), 3-ethoximinomethylbenzyl (I; b=0, $R_a$=$C_2H_5$—, D=H, n=0), α-cyano-3-ethoximinomethylbenzyl, α-cyano-3-methoximinoethylbenzyl (I, b=1, $R_a$=$CH_3$—, D=CN, n=0), the latter compounds being especially preferred when the oximino group is in the E configuration.

Esters I may be prepared by reaction of an acid $RCO_2H$ or an ester-forming derivative thereof with an intermediate of formula II

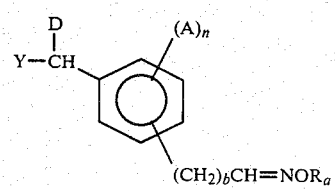

wherein Y represents a hydroxyl or halogen e.g. chlorine.

Intermediates of formula II, which are also included in a further aspect of the present invention, may be produced by 1. Protecting the aldehyde group in an appropriately substituted bromobenzaldehyde, converting Br to COOH by the Grignard route, releasing the aldehyde group and converting it to the oxime or alkoxime and reducing the COOH to $CH_2OH$. This $CH_2OH$ may be oxidised to CHO with pyridinium dichromate and the CHO group then reacted with HCN or monomagnesium acetylide to form the α-cyano or α-ethynyl benzyl alcohol.

2. Converting the CHO group in an appropriately substituted alkoxycarbonylbenzaldehyde to the oxime or alkoxime and then reducing the ester group to —$CH_2OH$ which, if required, can be converted into the α-cyano or α-ethynyl group as indicated above.

3. Protecting the aldehyde group in an appropriately substituted bromobenzaldehyde, converting Br to CHO in a Grignard synthesis using N-formyl piperidine, converting this CHO to the oxime or alkoxime, releasing the protected CHO and converting this to $CH_2OH$ by reduction or to CH(CN)OH or CH(C≡CH)OH by reaction with HCN or monomagnesium acetylide.

4. Compounds in which b=1 can be obtained starting from an appropriately substituted propenyl benzaldehyde having a protected CHO where the —$CH_2$—CH=$CH_2$ group is first converted to the oxime or alkoxime and the aldehyde group is then released and converted to the $CH_2OH$, CH(CN)OH or CH(C≡CH)OH by the methods indicated above.

Typical reaction schemes are set out below.

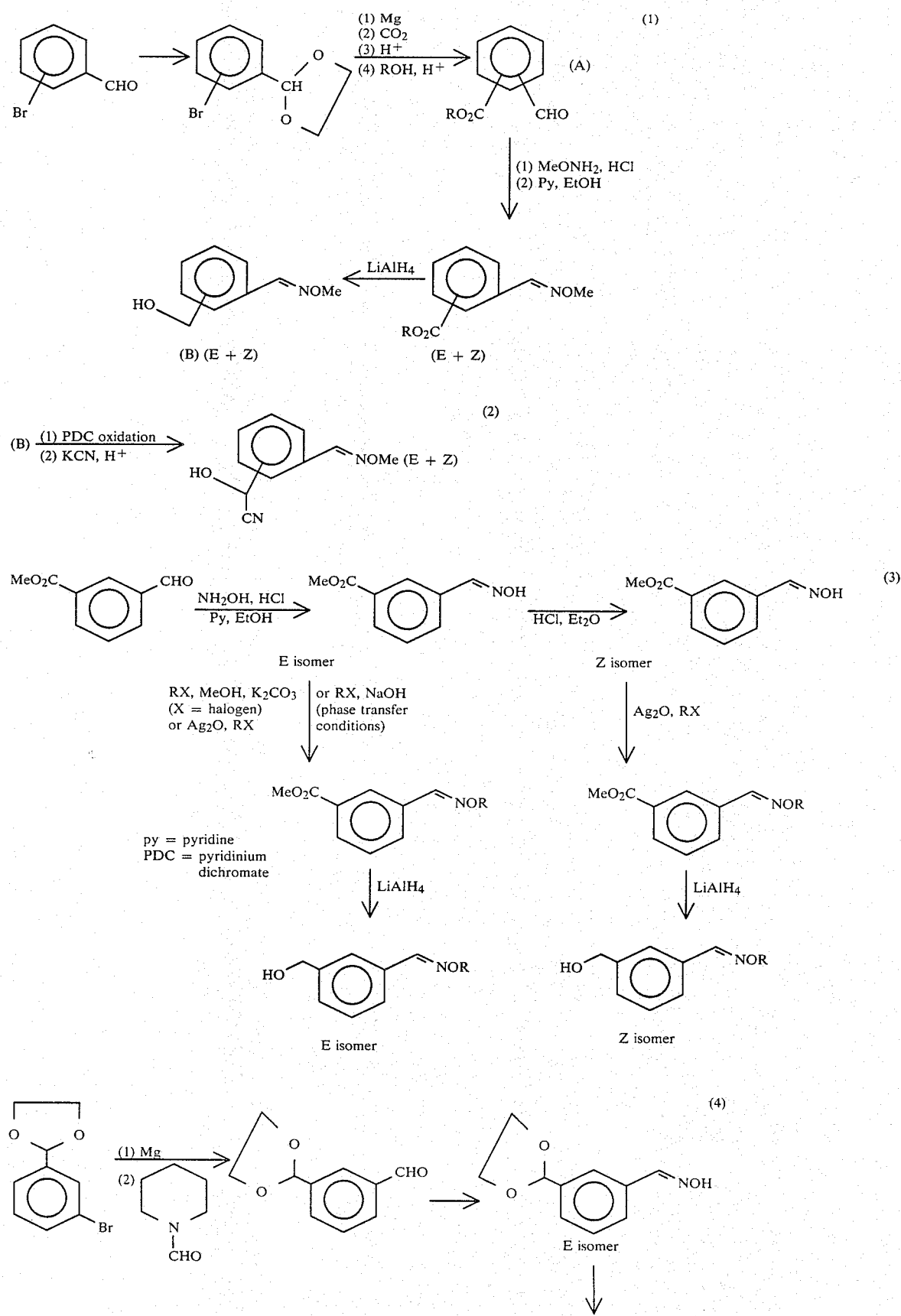

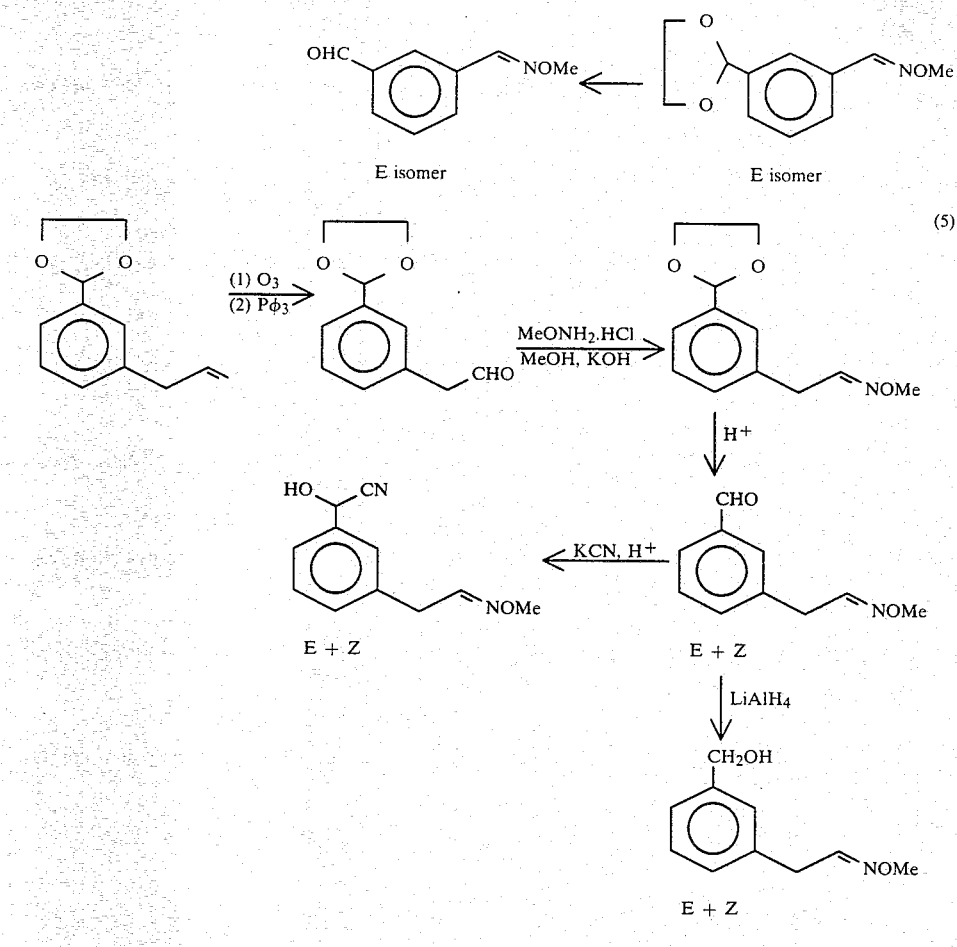

Intermediate cyanohydrins (II, Y=OH, D=CN) are generally produced from the corresponding aldehydes by treatment thereof with an alkali metal cyanide suitably under acidic conditions. The required aldehydes are usually obtainable by oxidation, e.g. PDC oxidation, of the corresponding alcohols.

Intermediates II in which Y represents halogen and D represents hydrogen may be produced from intermediates II in which Y represents —OH and D represents hydrogen in accordance with a further aspect of the present invention by treatment of the latter intermediates with a halogenating reagent of the class employed for conversion of carboxylic acids to acyl halides e.g. SO(hal)$_2$, typically with pyridine or P(hal)$_3$, hal representing chlorine or bromine.

In the compounds of formula I, R represents the residue of a carboxylic acid RCOOH which is an acid known to be capable of forming pesticidal compounds when esterified with α-cyano-3-phenoxybenzyl alcohol. There are a large number of carboxylic acids that are known to form pesticidal compounds of this type and these carboxylic acids fall, for the most part, into two clearly defined groups. The first group is the cyclopropane carboxylic acids which are the compounds where R is a group of the formula:

$$\begin{array}{c} R^1 \\ R^2 \end{array} \diagup\!\!\!\diagdown \begin{array}{c} \\ R^3 \quad R^4 \end{array} \qquad III$$

In formula III $R^3$ and $R^4$ will normally be an alkyl group, usually the same alkyl group, containing 1 to 4 carbon atoms and, as is well known in the art, dimethyl substitution normally gives high activity.

$R^2$ in formula III will normally be hydrogen or an alkyl group containing 1 to 4 carbon atoms and here the experience of the art indicates that $R^2$ will usually be hydrogen for maximum activity except in those compounds where $R^1$ is also an alkyl group, in which case $R^2$ preferably is an alkyl group, $R^1$, $R^2$, $R^3$ and $R^4$ all conveniently being the same alkyl group, e.g. methyl.

In formula III $R^1$ can be hydrogen or a substituted or unsubstituted acyclic or carbocyclic group. When $R^1$ is an unsubstituted hydrocarbyl group, it can be a straight chain or branched saturated or unsaturated acyclic or carbocyclic group such as an alkyl group, an alkenyl or alkadienyl group or a cycloalkyl, cycloalkylalkyl or cycloalkylalkenyl group. These hydrocarbyl groups preferably contain up to 10, particularly up to 6 carbon atoms.

When group $R^1$ is substituted, it is preferably one of the hydrocarbyl groups mentioned above which is substituted by one or more halogeno groups which may be fluorine, chlorine or bromine or by an alkoxy or oximino group or alkoxycarbonyl group, as in a group $R^1$ of particular interest of formula $—CH═CHCO_2R_x$ wherein $R_x$ represents an alkyl group typically containing 1 to 4 carbon atoms. When the substituents are two or more halogeno substituents, the halogeno substituents need not necessarily be the same halogen while when alkoxy groups are present, these preferably contain up to 4 carbon atoms and will normally be methoxy groups.

One particularly valuable structure for the group $R^1$ is of formula IV

                                                            IV where $R^7$ and $R^8$, which may be the same or different, are each an alkyl group containing 1 to 4 carbon atoms, a trifluoromethyl group or a halogeno group, which may be the same or different and are preferably fluorine, chlorine or bromine. One of $R^7$ and $R^8$ may also represent hydrogen or a phenyl or substituted phenyl group. Alternatively, $R^7$ and $R^8$ may together form a straight or branched substituted or unsubstituted saturated or unsaturated divalent hydrocarbon chain which may be substituted by one or more hetero atoms e.g. O, N or S, so that $R^7$ and $R^8$ together with the carbon atom to which they are attached form a carbocyclic or heterocyclic ring which will preferably contain 5 to 7 ring atoms, optionally 1 or 2 carbon-to-carbon double bonds and optionally one or more alkyl ($C_1$–$C_4$) or halogeno substituents on the cycloaliphatic ring. Other compounds of interest are those in which R is a group of the structure

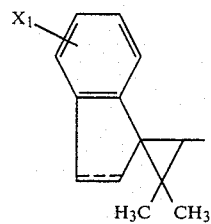

where the dotted line represents an optional double bond and $X_1$ represents H or halogen such as chlorine.

Specific cyclopropane carboxylic acids from which the compounds I of the present invention may be structurally derived include the following:
Chrysanthemic acid including particularly (1R)-trans chrysanthemic acid;
Pyrethric acid;
Dimethylcyclopropane carboxylic acid;
Trimethylcyclopropane carboxylic acid;
Tetramethylcyclopropane carboxylic acid;
2,2-Dimethyl-3-(cyclopentylidenemethyl)cyclopropane carboxylic acid;
2,2-Dimethyl-3-(2,2-dibromovinyl)cyclopropane carboxylic acid; particularly the (1R)-cis isomer thereof;
2,2-Dimethyl-3-(2,2-dichlorovinyl)cyclopropane carboxylic acid; particularly the (1R)-cis isomer thereof;
2,2-Dimethyl-3-(1,2,2,2-tetrabromoethyl)cyclopropane carboxylic acid;
2,2-Dimethyl-3-(1,2-dibromo-2,2-dichloroethyl)cyclopropane carboxylic acid;
2,2-Dimethyl-3-(2-chloro-3,3,3-trifluoropropenyl)cyclopropane carboxylic acid;
2,2-Dimethyl-3-(tetrahydro-2-oxo-thien-3-ylidenemethyl)cyclopropane carboxylic acid.

The second major class of carboxylic acids from which the esters of formula I may be structurally derived are the -substituted aryl acetic acid esters. In these compounds R in formula I will normally be of the structure

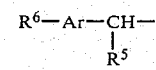
                                                            V wherein Ar represents a divalent aryl residue, $R^5$ represents a saturated or unsaturated straight chain or branched acyclic or cyclic hydrocarbon residue and $R^6$ represents hydrogen or one or more alkyl, alkoxy (including substituted alkoxy such as $OCF_3$ and $OCHF_2$) or halogeno substituents.

Ar will normally be an aryl residue based on a benzene ring although other aryl residues, e.g. polynuclear residues are also of interest. $R^5$ will normally be a saturated straight or branched chain hydrocarbon group particularly an alkyl group containing up to 8 carbon atoms and it is often desirable that this alkyl group should contain at least one secondary carbon atom particularly when that secondary carbon atom is directly bonded to the carbon atom directly bonded to the $R^6$ substituted aryl group. Thus $R^5$ is preferably an isopropyl group or a secondary butyl group. $R^5$ can also be a cycloaliphatic residue, again preferably containing a secondary carbon atom located immediately adjacent to the carbon atom carrying the $R^6$ substituted phenyl group, e.g. $R^5$ may be a cyclopropyl group or an alkyl substituted cyclopropyl group. $R^5$ can also be a cycloalkylalkyl group.

$R^6$ is preferably one or more halogeno or halogen-containing substituents, e.g. F, Cl, Br or $OCHF_2$ or $OCF_3$ and, when more than one halogeno or halogen-containing substituent is present, they will normally be but are not necessarily the same halogen. When $R^6$ is an alkyl or alkoxy group, these preferably contain up to 4 carbon atoms and again, when more than one such group is present, they need not necessarily be the same groups. When only one substituent $R^6$ is present, it is preferably present in the para-position. When more than one $R^6$ substituent is present, the para-position is preferably substituted together with one or more of the ortho- and meta-positions.

Another class of carboxylic acids from which the esters of the present invention may be structurally derived are -substituted arylamino acetic acids of the type

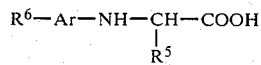

where $R^5$, $R^6$ and aryl are as defined above.

Specific α-substituted phenyl acetic acids from which esters of the formula I may be structurally derived include:
α-Isopropyl-p-chlorophenyl acetic acid;
α-Cyclopropyl-p-chlorophenyl acetic acid;
α-Cyclopropyl-p-methylphenyl acetic acid;
α-Isopropyl-p-(difluoromethoxy)-phenyl acetic acid;

α-Isopropyl-(2-chloro-4-trifluoromethyl anilino)acetic acid.

The compounds of the invention exhibit optical isomerism in that the carbon atom bearing the substituent D can exist in the R or S configuration and the present invention includes compounds in which the configuration is substantially completely R or in which the configuration is substantially completely S or mixtures thereof.

Compounds of the invention in which R represents a substituted cyclopropane residue of formula III can exist in the form of both geometrical and optical isomers. This is because of the unsymmetrical substitution at $C_1$ and $C_3$ of the cyclopropane ring. Compounds of the present invention include those isomers in which the hydrogen atoms at $C_1$ and $C_3$ of the cyclopropane ring are substantially completely in the cis configuration or substantially completely in the trans configuration or mixtures thereof. The present invention also includes compounds in which the configuration at $C_1$ is substantially completely R or substantially completely S and mixtures thereof. In the compounds of the invention in which R represents a group of formula III, the optical configuration at $C_1$ and $C_3$ cannot vary independently of the geometrical configuration of the hydrogen atoms at $C_1$ and $C_3$ of the cyclopropane ring. The effect of this is that the configuration of the cyclopropane ring can be defined uniquely by specifying the optical configuration at $C_1$ and the geometrical configuration of the hydrogen atoms at $C_1$ and $C_3$ and, for definition purposes, we have adopted nomenclature of the form (1R)-cis, (1R)-trans etc. it being unnecessary to specify the optical configuration at $C_3$ which is fixed once the other two variables are defined. Adopting this nomenclature avoids the confusion which can arise by having to designate either R or S to the same optical configuration at $C_3$ depending upon the nature of the substituents on the cyclopropane ring and even those on the side chain.

When R is a group of formula III in which $R^1$ is a group of formula IV in which the substitution about the ethylenic bond is asymmetrical, that is to say $R^7 \neq R^8$ then the configuration of this part of the molecule can be substantially completely in the E form or substantially completely in the Z form or a mixture thereof.

When R is a group of formula V, the carbon atom to which $R^5$ is bonded can exist substantially completely in the S configuration or substantially completely in the R configuration or can be a mixture of the two forms.

The compounds of the present invention can be in the form of single isomers but, having regard to the fact that the compounds have at least one and frequently more than one centre of asymmetry, the compounds of the invention will normally be in the form of isomer mixtures although these isomer mixtures can be optically active and/or substantially completely in one geometric form.

The compounds of the present invention can be prepared by an esterification involving the reaction of an alcohol of formula II or an esterifiable derivative thereof with a carboxylic acid of formula RCOOH or an esterifiable derivative thereof. It is usually convenient in practice to react an alcohol of formula II with an acyl chloride of formula RCOCl or to react a salt of the carboxylic acid, e.g. a silver or triethylammonium salt with a benzylhalide derivative, that is to say a monohaloalkylbenzyl or cyanobenzyl halide which may be ring alkylated or to esterify the carboxylic acid with the alcohol in the presence of dicyclohexyl carbodi-imide and a catalyst.

Alternatively, the esters of the invention can be prepared by transesterification by reacting a $C_1$–$C_6$ alkyl ester of the carboxylic acid with a benzyl alcohol of formula II in the presence of a basic transesterification catalyst. This method is not usually satisfactory where the molecule contains another base-sensitive residue, e.g. where the carboxylic acid is pyrethric acid.

A further possibility for synthesis is to prepare an intermediate ester by the methods described above replacing the compound of formula II by a compound in which the —$(CH_2)_b$CH=NORa group is replaced by a CHO or a protected CHO or a —$CH_2.CH$=$CH_2$ group which is converted, in the intermediate ester, to the —$(CH_2)_b$CH=NORa group by one of the methods mentioned above for the production of intermediates II.

One or more of the esters of formula I can be formulated with an inert carrier or diluent to give pesticidal or knock down compositions and such compositions form a further aspect of the present invention. These compositions can be in the form of dusts and granular solids, wettable powders, mosquito coils, vapour mats and other solid preparations, or as emulsions, emulsifiable concentrates, sprays and aerosols and other liquid preparations after the addition of the appropriate solvents, diluents and surface-active agents.

Compositions formulated in a manner suitable for controlling soil pests typically by treatment of the soil are of special interest. For this purpose compositions containing compounds I hereinbefore described are particularly suitable as they generally have lower molecular weights than many previously described pyrethroids, and it is envisaged that their relatively high vapour pressures allow them to diffuse through the soil.

The pesticidal compositions of the invention will normally contain from 0.001 to 25% by weight of the compound of formula I but the compositions can contain higher concentrations of active ingredient of formula I e.g. up to 95% for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants and other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists of the type known to be capable of synergising the activity of natural pyrethrin and pyrethroid-like insecticides. Synergists of this type include piperonyl butoxide, tropital and sesamex.

The compounds of formula I can be used to control pest infestation in the domestic, horticultural or agricultural or medical, including veterinary, areas and in such pest control advantage can be taken of knock-down properties present in the compounds of the invention. The compounds or compositions of the invention can be used to combat pest infestation by treating pests or surfaces or environments susceptible to pest infestation with effective amounts of the active compounds of formula I or of compositions containing them. For example, they may be used in a domestic environment for spraying rooms to combat infestation with houseflies or other insects, they can be used for treatment of stored dry crops or cereals to combat infestation by insects or other pests, they can be used to spray growing crops, e.g. cotton or rice to combat infestation by common pests and they can be used in a medical or veterinary field, e.g. as a cattle spray to prevent or treat infestation by insects or other pests.

Knock-down compositions or fumigatory compositions can be prepared as aerosols or as mosquito coils or as vapour mats. For example, a pure spray to control both flying insects and crawing insects e.g. cockroaches, can be formulated from an invention compound together with a known pyrethroid which is an air kill compound e.g. permethrin, cypermethrin or deltamethrin. These active compounds may be formulated with conventional solvents and aerosol propellants using 0.05 to 95% by weight of active ingredients. The fumigatory composition may contain 0.05 to 10% w/w active compound formulated as a coil or spiral with a combustible support, pyrethrum residue, Tabu powder (*Machilus thumbergii* leaves), pyrethrum stalk powder, ceader leaf powder, wood powder e.g. pine sawdust, starch and coconut shell powder being typical materials for use in the formulations. Alternatively, the active compound can be formulated on a non-combustible fibrous support which can then be heated e.g. electrically, to vaporise the active compound.

Although, as hereinbefore indicated, they are of particular interest for the disinfestation of soil to control pests such as the onionfly, *Delia antiqua*, the compounds may find application in the control of a wide variety of pests including:

from the class of the Isopoda, for example *Oniscus asellus*, *Armadillidium vulgare* and *Porcellio scaber*;

from the class of the Diplopoda, for example *Blaniulus guttulatus*;

from the class of the Chilopoda, for example *Geophilus carpophagus* and Scutigera spec.;

from the class of the Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis*, *Periplaneta americana*, *Leucophaea madarae*, *Blattela germanica*, *Acheta domesticus*, Gryllotalpa spp., *Locusta migratoria migratorioides*, *Melanoplus differentialis* and *Schistocerca gregaria*;

from the order of the Dermaptera, for example *Forficula auricularia*;

from the order of the Isoptera, for example Reticulitermes spp.;

from the order of the Anoplura, for example *Phylloxera vastatrix*, Pemphigus spp., *Pediculus humanus corporis*, Haematopinus spp. and Linognathus spp.;

from the order of the Mallophaga, for example Trichodectes spp. and Demalinea spp.;

from the order of the Thysanoptera, for example *Hercinothrips femoralis* and *Thrips tabaci*;

from the order of the Heteroptera, for example Eurygaster spp., *Dysdercus intermedius*, *Piesma quadrata*, *Cimex lectularius*, *Rhodnius prolius* and Triatoma spp.;

from the order of the Homoptera, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, Myzus spp., *Phorodon humuli*, *Rhopalosiphum padi*, Empoasca spp., *Euscelis bilobatus*, *Nephotettix cincticeps*, *Lecanium corni*, *Saissetia oleae*, *Laodelphax striatellus*, *Nilaparvata lugens*, *Aondiiella aurantii*, *Aspidiotus hederae*, Pseudococcus spp. and Psylla spp.;

from the order of the Lepidoptera, for example *Pectinophora gossypiella*, *Bupalus piniarius*, *Cheimatobia brumata*, *Lithocolletis blancardella*, *Hyponomeuta padella*, *Plutella maculipennis*, *Malacosoma neustria*, *Euproctis chrysorrhoea*, Lymantria spp., *Bucculatrix thurberiella*, *Phyllocnistis citrella*, Agrotis spp., Euxoa spp., Feltia spp., *Earias insulana*, Heliothis spp., *Laphygma exigua*, *Mamestra brassicae*, *Panolis flammea*, *Prodenia litura*, Spodoptera spp., *Trichoplusia ni*, *Carpocapsa pomonella*, Pieris spp., Chilo spp., *Pyrausta nubilalis*, *Ephestia kuehniella*, *Galleria mellonella*, *Cacoecia podana*, *Capua reticulana*, *Choristoneura fumiferana*, *Clysia ambiguella*, *Homona magnanima* and *Tortrix viridana*;

from the order of the Coleoptera, for example *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, Diabrotica spp., *Psylliodes chrysocephala*, *Epilachna varivestis*, Atomaria spp., *Oryzaephilus surinamensis*, Anthonomus spp., Sitophilus spp., *Otiorrhynchus sulcatus*, *Cosmopolites sordidus*, *Ceuthorrhynchus assimilis*, *Hypera postica*, Dermestes spp., Trogoderma spp., Anthrenus spp., Attagenus spp., Lyctus spp., *Meligethes aeneus*, Ptinus spp., *Niptus hololeucus*, *Gibbium psylloides*, Tribolium spp., *Tenebrio molitor*, Agriotes spp., Conoderus spp., *Melolontha melolntha*, *Amphimallon solstitialis* and *Costelytra zealandica*;

from the order of the Hymenoptera, for example Diprion spp., Hoplacampa spp., Lasius spp., *Monomorium pharaonis* and Vespa spp.;

from the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus*, *Oscinella frit*, Phorbia spp., *Pegomyia hyoscyami*, *Ceratitis capitata*, *Dacus cleae* and *Tipula paludosa*;

from the order of the Siphonaptera, for example *Xenopsylla cheopis* and Ceratophyllus spp.;

from the class of the Arachnida, for example *Scorpio maurus* and *Latrodectus mactans*;

from the order of the Acarina, for example *Acarus siro*, Argas spp., Ornithodoros spp., *Dermanyssus gallinae*, *Eriophyes ribis*, *Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The invention is illustrated by the following Examples in which temperatures are in °C. and:

$C_R$ represents the acid residue

R in compound I: (IR)-trans:chrysanthemyl $B_R$ represents the acid residue

R in compound I: (IR)-cis-3-(2,2-dibromovinyl)-2,2-dimethylcyclopropane carboxyl In Examples 1–18 the oximino group $(CH_2)_b.CH=N-ORa$ is in position 3 on the ring while in Examples 19–22 it is in position 4.

EXAMPLE 1

(Compound I: D=H, n=0, b=0 $R_a$=Et, E isomer, R=$B_R$)

3-carbomethoxybenzaldehyde (3 g), hydroxylamine hydrochloride (3 g), pyridine (3 ml) and absolute ethanol (30 ml) are refluxed for 1 hour and cooled. The solvent is evaporated from the reaction mixture, dilute hydrochloric acid is added and after stirring the mixture is extracted three times with diethyl ether. The extract is dried and the ether evaporated, leaving the oxime (E isomer) melting point 107°–108°, 3.5 g.

The latter oxime (0.5 g), ethyl iodide (15 ml) and dry potassium carbonate (1.6 g) are refluxed overnight. The mixture is then poured onto water and extracted with methylene dichloride (three times) after which the solvent is evaporated to leave a quantitative yield of the ethyl oxime ether, $n_D^{20}$ 1.5392.

The ethyl oxime ether (0.5 g), lithium aluminium hydride (0.1 g) and dry diethyl ether (about 20 ml) are stirred at room temperature for one hour. Water (0.1 ml) is added followed by 15% sodium hydroxide (0.1 ml), and then further water (0.3 ml). The mixture is stirred for five minutes, filtered, dried and the solvent evaporated. The product is produced in quantitative yield as a semi-solid.

Esterification. To a stirred solution of the latter alcohol (0.79 mmol) and pyridine (0.08 g, 1 mmol) in dry benzene (10 ml) at room temperature is added (1R cis)-2,2-dimethyl-3(2,2-dibromovinyl)cyclopropane carboxylic acid chloride (0.25 g, 0.79 mmol). After three hours the mixture is concentrated under vacuum and subjected to a thin layer of chromotography on silica eluted with 15% diethyl ether in petroleum ether b.p. 60°–80° to yield the ester $n_D^{20}$ 1.5316.

EXAMPLE 2

(Compound I: D=H, n=0, b=0, $R_a$=Et, E isomer, R=$C_R$)

The oxime ether alcohol of Example 1 (II, Y=OH, D=H, n=0, b=0 and $R_a$=Et; E isomer) is esterified with 1R trans chrysanthemyl chloride by the method of Example 1 to yield the ester $n_D^{20}$ 1.5250.

EXAMPLE 3

(Compound D=H, n=0, b=0 $R_a$=Et, Z isomer, R=$B_R$)

The 3-carbomethoxybenzaldoxime of Example 1 (E isomer) (0.78 g) is stirred in dry diethyl ether (20 ml) and hydrogen chloride gas is bubbled through the mixture for 10 minutes after precipitation has begun. The mixture is filtered and the residue washed with dry diethyl ether. The residue is placed in a separating funnel with ether and concentrated aqueous potassium carbonate added until effervescence ceases following which the ether layer is separated, dried and the ether removed to yield 0.54 g of solid 3-carbomethoxybenzaldoxime (Z isomer) melting point 117°–119°.

The oxime (0.54 g) is treated with ethyl iodide (approximately 8 ml) and wet silver oxide (approximately 1.6 g) and the mixture stirred at room temperature. The mixture is then refluxed for one hour, filtered, the residue washed with methylene chloride and the solvent evaporated to yield the ethyl oxime ether, 0.64 g, $n_D^{20}$ 1.5378.

The latter compound (0.5 g) is stirred at room temperature for 20 minutes with lithium aluminium hydride (0.1 g) in dry diethyl ether (approximately 20 ml). Water (0.1 ml) is added, followed by 15% sodium hydroxide (0.1 ml) and by further water (0.3 ml). The mixture is then stirred, filtered and the solvent evaporated to yield the alcohol, $n_D^{20}$ 1.5387, 0.5 g).

Esterification

The latter alcohol is esterified with (1R cis) 2,2-dimethyl-3-(2,2-dibromovinyl)cyclopropane carboxylic acid chloride following the method of Example 1 to yield the ester, $n_D^{20}$ 1.5315.

EXAMPLE 4

(Compound I: D=H, n=0, b=0, $R_a$=Et, Z isomer, R=$C_R$)

The alcohol of Example 3 is esterified by following the procedure of Example 1 but using 1R trans-chrysanthemyl chloride and using an alumina column, eluting with benzene, in place of t.l.c., for purification, to yield the ester, $n_D^{20}$ 1.5248.

EXAMPLE 5

(Compound I: D=H, n=0, b=0, $R_a$=Me, E+Z isomer mixture, R=$B_R$)

3-carbomethoxy benzaldehyde (2 g) is mixed with pyridine (2.2 g), methoxyamine hydrochloride (2.2 g) in a mixture of dioxane (30 ml) and water (5 ml) and the mixture is refluxed with stirring for 2 hours. The mixture is then cooled, poured into dilute hydrochloric acid and extracted with methylene chloride twice, the extract is dried and the solvent evaporated to yield the methyl oxime ether (1.8 g) (1:1). The latter compound is reduced with lithium aluminium hydride following the procedure of Example 1 to give the corresponding alcohol, $n_D^{20}$ 1.5660. Esterification is carried out by following the procedure of Example 1 to yield the ester $n_D^{20}$ 1.5738.

EXAMPLE 6

(Compound I: D=H, n=0, b=0, $R_a$=Me, E+Z isomer mixture, R=$C_R$)

The alcohol of Example 5 is esterified by following the procedure of Example 1 but using 1R trans-chrysanthemyl chloride to yield the ester $n_D^{20}$ 1.5322.

EXAMPLE 7

(Compound I: D=H, n=0, b=0, $R_a$=Me, E isomer R=$B_R$).

The compound $n_D^{20}$ 1.5713 is prepared by esterifying, following the procedure of Example 1, the alcohol produced by following procedure 1 but using methyl iodide in place of ethyl iodide.

EXAMPLE 8

(Compound I: D=H, n=0, b=0, $R_a$=Me, E isomer, R=$C_R$).

The alcohol of Example 7 is esterified by following the procedure of Example 1 using 1R trans-chrysanthemyl chloride to yield the ester, $n_D^{20}$ 1.5310.

EXAMPLE 9

(Compound I: D=H, n=0, b=1, $R_a$=Me, (E+Z 1:1) R=$C_R$)

The ethylene acetal of 3-bromobenzaldehyde (10 g) is converted into the Grignard reagent by reaction with magnesium (1.13 g) in dry THF (ca. 250 ml). Cuprous bromide (0.9 g) is added and the mixture is cooled in cardice. Allylbromide (8.52 g) in dry THF is then added and the mixture is stirred overnight following which saturated ammonium chloride is added, the mixture is extracted with diethyl ether (3 times), the ether extract is washed, dried and the solvent evaporated to yield the crude ethylene acetal of 3-allylbenzaldehyde (8 g).

The ethylene acetal (8 g) is dissolved in dry methylene chloride (approximately 120 ml) and cooled in cardice. A calculated excess of an ozone-oxygen mixture is bubbled through the solution (the solution does not turn blue) following which the solution is flushed with oxygen for 15 minutes and then nitrogen for 15 minutes while cooled in the cardice bath. Triphenylphosphine (12 g) is then added and the mixture is allowed to warm to room temperature over 1 hour. The solvent is then evaporated off and the triphenylphosphine oxide produced is precipitated out with ether (twice). The residue is then distilled directly under 0.04 mm Hg, bp 120°–125° to yield 5 g of the ethylene acetal of 3-formyl phenyl acetaldehyde.

To a stirred solution of methoxylamine hydrogen chloride (0.66 g) in A.R. methanol (25 ml) at room temperature is added methanolic potassium hydroxide (0.44 g potassium hydroxide in 2.5 ml methanol) and the mixture is stirred for 15 minutes, potassium chloride precipitating out. The latter aldehyde (1 g) is dissolved in 10 ml methanol, added and the mixture refluxed for five minutes and then stirred for 10 minutes. Water is then added and the mixture concentrated on a rotary evaporator. Water is added and the residue extracted with ether three times following which the extracts are washed with water, dried and the solvent evaporated off to yield 1.15 g of methyl oxime ether of the ethylene acetal of 3-formylphenylacetaldehyde (E+Z isomer mixture) $n_D^{20}$ 1.5638.

The latter acetal (1.1 g) is dissolved in diethyl ether (40 ml) and a mixture of hydrochloride acid and water (1:1, 20 ml). The mixture is stirred for half an hour and the aqueous layers then extracted with ether twice, the ethereal layers combined and washed with water, dried and the solvent evaporated off to yield 0.62 g of the crude methyl oxime ether of 3-formylphenylacetaldehyde (E+Z isomer mixture), $n_D^{20}$ 1.579.

The formyl group of the latter oxime ether is reduced by lithium aluminium hydride following the procedure of Example 1 to yield the alcohol, $n_D^{20}$ 1.5128.

Esterification following the procedure of Example 1 with IR-trans chrysanthemyl chloride yields the ester, $n_D^{20}$ 1.5190.

EXAMPLE 10

(Compound I: D=H, n=0, b=1, $R_a$=Me (E+Z, 1:1), R=$B_R$)

Esterification of the alcohol of Example 9 following the procedure of Example 1 yields the ester $n_D^{20}$ 1.5604.

EXAMPLE 11

(Compound I: D=CN, n=0, b=0, $R_a$=Me, (E isomer, R=$B_R$)

To a suspension of flame dried magnesium turnings (2.1 g) in dry THF (20 ml) under nitrogen is added dropwise a solution of the ethylene acetal of 3-bromobenzaldehyde (20 g) in small portions. When the magnesium has completely reacted the mixture is cooled in a water bath and N-formyl piperidine (12 g) dissolved in dry diethyl ether (30 ml) is added slowly. The mixture is then refluxed for five minutes, cooled in a water bath and saturated ammonium chloride is added slowly. Most of the THF is removed on a rotary evaporator and the mixture is extracted with diethyl ether three times, washed with water, dried over anhydrous sodium sulphate and evaporated. The residue is distilled under 0.03 mm Hg, b.p. 98°–100° to yield 8.2 g (53%) of the ethylene acetal of 3-formyl benzaldehyde, $n_D^{20}$ 1.5503.

The latter acetal (1 g) is added with stirring to a mixture of hydroxylamine hydrochloride (2.1 g), sodium hydroxide (1.26 g) water (5 ml) and ethanol (15 ml) following which the mixture is refluxed for four hours and cooled overnight. The solvent is then evaporated off, water is added and the mixture extracted with diethyl ether three times. The residue is then acidified with approximately 2N hydrochloric acid to pH about 6–7 and then extracted three times with diethyl ether. After drying, removal of the solvent yields the oxime (E isomer) as an oil (1.0 g, $n_D^{20}$ 1.5672).

The latter oxime (0.5 g) is mixed with sodium hydroxide (0.11 g) in water (5 ml) and the mixture stirred until homogeneous. Methyl iodide (3 ml), a phase transfer catalyst (tetrabutylammonium bromide, 10 mg) are then added and the mixture is refluxed for one hour with vigorous stirring. The organic layer is then filtered through a "sep-pack" cartridge (Waters Associates), eluting with diethyl ether. Filtration is repeated on the ethereal extract of the aqueous phase and the ether evaporated from the combined ethereal layers on a rotary evaporator to leave the methyl oxime ether (E isomer) as a clear oil, $n_D^{20}$ 1.5532, 0.5 g.

The latter oxime ether (0.5 g) is mixed with diethyl ether (10 ml), concentrated hydrochloric acid (5 ml) and water (5 ml) and stirred vigorously at room temperature for about 45 minutes. The ether layer is then separated and the aqueous layer extracted with diethyl ether twice. The combined ethereal extracts are washed with saturated sodium chloride, dried and the solvent evaporated off to yield the methyl oxime ether of 3-formyl benzaldoxime (E isomer), 0.25 g.

The latter compound (0.35 g) is mixed with water (1 ml), potassium cyanide (0.06 g) and tetrahydrofuran (6 ml) and the mixture is cooled in an ice-salt bath at a temperature maintained below 5° C. during addition of sulphuric acid (40%, 1.3 ml). The mixture is then warmed to room temperature over half an hour and then poured onto water, extracted with ether and the extract dried and the solvent evaporated. The product (II: Y=OH, D=CN, n=0, b=0, $R_a$=Me; E isomer), 0.43 g is a white solid mp 69°–70°.

Esterification using the procedure of Example 1 yields the ester, $n_D^{20}$ 1.5668.

EXAMPLE 12

(Compund I: D=CN, n=0, b=0, $R_a$=Me, E isomer, R=$C_R$)

Esterification is performed as in the previous Example but using (1R) trans-chrysanthemyl chloride to yield the ester $n_D^{20}$ 1.5354.

EXAMPLE 13

(Compound I: D=CN, n=0, b=0, $R_a$=Me E+Z isomer mixture, R=Br)

The alcohol of Example 5 (2.3 g) is mixed with pyridinium dichromate and dry methylene chloride (100 ml) and the mixture is stirred under nitrogen overnight. Petroleum ether (50 ml) and diethyl ether (50 ml) are then added, the mixture is stirred and then filtered through a pad of celite/charcoal. Evaporation of the solvent yields the corresponding aldehyde (1.8 g).

The aldehyde is converted into the corresponding cyanohydrin by following the procedure of Example 11.

Esterification following the procedure of Example 1 yields the ester, $n_D^{20}$ 1.5388.

EXAMPLE 14

(Compound I: D=CN, n=0, b=0, $R_a$=Me E+Z isomer mixture, R=$C_R$)

Esterification of the cyanohydrin of Example 13, following the procedure of Example 1, but using 1 trans-chrysanthemyl chloride yields the ester $n_D^{20}$ 1.5282.

EXAMPLE 15

(Compound I: D=CN, n=0, b=1, $R_a$=Me, E+Z isomer mixture, R=$B_R$)

The methyl oxime ether of 3-formylphenylacetaldehyde (E+Z isomer mixture) is produced by the procedure of Example 9.

The latter compound (0.2 g) is mixed with water (1 ml), potassium cyanide (0.6 g) and tetrahydrofuran (6 ml), cooled in an ice-salt bath and the temperature maintained below 5° C. while sulphuric acid (40% 1.3 ml) is added. The mixture is then warmed to room temperature over half an hour, poured onto water and extracted with ether three times. The extract is washed with water, dried and the solvent evaporated off to yield 0.22 g of alcohol (II, Y=OH, D=CN, n=0, b=1, $R_a$=Me, E+Z isomer mixture), $n_D^{20}$ 1.5628.

Esterification is performed as in Example 1, using (1R cis)-2,2-dimethyl-3-(2,2-dibromovinyl) cyclopropane carboxylic acid chloride to yield the ester, $n_D^{20}$ 1.5449.

EXAMPLE 16

(Compound I: D=CN, n=0, b=1, $R_a$=Me, E+Z isomer mixture, R=$C_R$)

Esterification is performed as in the previous Example but using 1R trans chrysanthemyl chloride to yield the ester $n_D^{20}$ 1.5212.

EXAMPLE 17

(Compound I: D=CN, n=0, b=0, $R_a$Et, E isomer R=$B_R$)

The ester is produced by following the procedure of Example 11 but using ethyl iodide in place of methyl iodide.

EXAMPLE 18

(Compound 1, D=CN, n=0, b=0, $R_a$=Et, E isomer, R=$C_R$)

The ester is produced by esterifying the cyanohydrin of Example 17 following the procedure of Example 1, using 1R trans-chrysanthemyl chloride.

EXAMPLE 19

(Compound I, D=H, n=2, b=o, $R_a$=Me (E isomer), $A_n$=2,6-dimethyl, R=$C_R$)

The ethylene acetal of 2,6-dimethyl-4-bromobenzaldehyde, m.p. 99°-101° C., prepared by reacting the aldehyde with 1,2-bis-(trimethylsilyloxy)ethane in the presence of trimethylsilylmethyl trifluoromethane sulphonate, was converted following the procedure of Example 11 to the ethylene acetal of 2,6-dimethyl-4-formyl benzaldehyde, then directly to the E methoxime of the ethylene acetal of 2,6-dimethyl-4-formyl benzaldehyde following the procedure of Example 9 using methoxyamine. The protecting acetal group was then removed as described in Example 11 and the resulting E-methoxime of 2,6-dimethyl-4-formyl benzaldehyde reduced to alcohol II which is the E-methoxime of 2,6-dimethyl-4-hydroxymethyl benzaldehyde. Esterification of the alcohol with 1R,trans chrysanthemoyl chloride by the procedure described in Example 2 gave the title ester, mp 61°-63°.

EXAMPLE 20

(Compound I, D=H, n=2, b=o, $R_a$=Me (E isomer), $A_n$=2,6-dimethyl, R=$B_r$)

The alcohol II prepared as described in Example 19 was esterified with 1R,cis-2,2-dimethyl-3-(2,2-dibromovinyl)cyclopropane carboxylic acid chlorine as described in Example 1 to give the title ester, m.p. 102°-104°

EXAMPLE 21

(Compound I, D=CN, n=2, b=o, $R_a$=Me (E isomer), $A_n$=2,6-dimethyl, R=$C_R$)

The E-methoxime of 2,6-dimethyl-4-formyl benzaldehyde, obtained as described in Example 19, is reacted with potassium cyanide by the procedure described in Example 11 to alcohol II which is the E-methoxime of 2,6-dimethyl-4-(α-cyano)-hydroxymethylbenzaldehyde. This alcohol is then esterified with 1R,trans chrysanthemoyl chloride as described in Example 2 to give the title ester $n_D^{20}$ 1.5214.

EXAMPLE 22

(Compound I, D=CN, n=2, b=o, $R_a$=Me (E isomer), $A_n$=2,6-dimethyl, R=$B_r$)

The α-cyano alcohol described in Example 21 is esterified with 1R,cis-2,2-dimethyl-3-(2,2-dibromovinyl)-cyclopropane carboxylic acid chloride by the procedure described in Example 1 to give the title ester as a semi solid.

The pesticidal activity is assessed against houseflies and mustard beetles by using the following techniques:

Houseflies (*Musca domestica*)

Female flies are treated on the thorax with a one microliter drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. $LD_{50}$ values are calculated in micrograms of insecticide per fly and relative toxicities are calculated from the inverse ratios of the $LD_{50}$ values (see Sawicki et al., Bulletin of the World Health Organisation, 35, 893, (1966) and Sawicki et al., Entomologia and Exp. Appli. 10 253, (1967)).

Mustard Beetles (*Phaedon cochleariae* Fab)

Acetone solutions of the test compound are applied ventrally to adult mustard beetles using a micro drop applicator. The treated insects are maintained for 48 hours after which time kill is assessed. Two replicates of 40 to 50 mustard beetles are used at each dose level and 5 dose levels are used for each compound. Again, $LD_{50}$ values are calculated and relative potencies are calculated from the inverse ratios of $LD_{50}$ (see Elliott et al., J. Sci. Food Agric. 20, 561, (1969)).

Relative potencies are calculated by comparison with 5-benzyl-3-furylmethyl (1R)-trans-chrysanthemate (Bioresmethrin) which is one of the more toxic chrysanthemate esters known to house flies and mustard beetles, its toxicity being about 24 times that of allethrin to houseflies and 65 times that of allethrin to mustard beetles. Bioassay results are set forth in the Table.

TABLE

Compounds I $C_R$ = (IR)-trans chrysanthemyl
$B_R$ = (IR)-CIS-3-(2,2-dibromovinyl)-2,2-dimethylcyclopropanecarboxyl
$(A)_n$ = H; Position of —(CH$_2$)$_b$ CH=NOR$_a$ in ring: 3

| Example No. | D | $R_a$ | b | Configuration at —CH=NORa | R | Relative Potencies (Bioresmethrin = 100) | |
|---|---|---|---|---|---|---|---|
| | | | | | | HF | MB |
| 2 | H | Et | 0 | E | $C_R$ | 0.6 | 0.5 |
| 1 | H | Et | 0 | E | $B_R$ | 7.4 | 18 |
| 4 | H | Et | 0 | Z | $C_R$ | 0.5 | Ca 0.1 |
| 3 | H | Et | 0 | Z | $B_R$ | 5.1 | 5.1 |
| 6 | H | Me | 0 | E + Z (1:1) | $C_R$ | 2.8 | 1.5 |
| 5 | H | Me | 0 | E + Z (1:1) | $B_R$ | 8.8 | 7.9 |
| 8 | H | Me | 0 | E | $C_R$ | 7 | 3.4 |
| 7 | H | Me | 0 | E | $B_R$ | 20 | 20 |
| 9 | H | Me | 1 | E + Z (1:1) | $C_R$ | 1.5 | 2.5 |
| 10 | H | Me | 1 | E + Z (1:1) | $B_R$ | 22.7 | 13 |
| 14 | CN | Me | 0 | E + Z (1:1) | $C_R$ | 5.4 | 13 |
| 13 | CN | Me | 0 | E + Z (1:1) | $B_R$ | 9.1 | 23 |
| 12 | CN | Me | 0 | E | $C_R$ | 18 | 13 |
| 11 | CN | Me | 0 | E | $B_R$ | 23 | 69 |
| 16 | CN | Me | 1 | E + Z (1:1) | $C_R$ | 10 | 13 |
| 15 | CN | Me | 1 | E + Z (1:1) | $B_R$ | 9 | 41 |
| 18 | CN | Et | 0 | E | $C_R$ | 9.5 | 3.1 |
| 17 | CN | Et | 0 | E | $B_R$ | 8 | 19 |
| *19 | H | Me | 0 | E | $C_R$ | 1 | — |
| *20 | H | Me | 0 | E | Br | 2 | 4 |

*these are 2,6-dimethyl-4-methoximinomethyl compounds

We claim:

1. A compound of the formula:

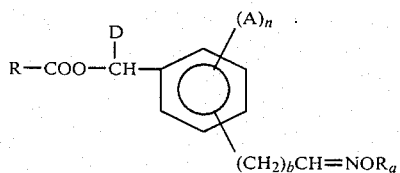

wherein

D represents hydrogen or a cyano group or an ethynyl group;
$R_a$ represents an alkyl group;
A represents an alkyl group or a halogen or trifluoromethyl group;
n is 0 or an integer of 1-4,
b is 0 or 1; and
R is selected from the group consisting of:

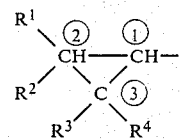 (a)

wherein
$R^3$ and $R^4$ each represent an alkyl group which may be the same or different;
$R^2$ represents hydrogen or an alkyl group; and
$R^1$ represents hydrogen or a substituted or unsubstituted acyclic or carbocyclic group; and

 (b)

wherein
Ar represents an aryl residue;
$R^5$ represents a saturated or unsaturated straight chain or branched acyclic or cyclic hydrocarbon residue; and
$R^6$ represents hydrogen or at least one alkyl, alkoxy, substituted alkoxy or halogen substituent; the $R^6$ groups, when more than one is present, being the same or different.

2. A compound according to claim 1 wherein the —(CH$_2$)$_b$CH=NOR$_a$ group is in the 3 position.

3. A compound according to claim 1 wherein $R_a$ represents methyl or ethyl.

4. A compound according to claim 1 wherein b is 0.

5. A compound according to claim 1 wherein n is 0.

6. A compound according to claim 1 wherein $R^3$ and $R^4$ each represent methyl.

7. A compound according to claim 1 wherein $R^1$ represents an unsubstituted alkyl, alkenyl or alkadienyl group or an alkyl, alkenyl or alkadienyl group substituted by at least one halogeno, alkoxy, oximino or alkoxy carbonyl group.

8. A compound according to claim 1 wherein $R^2$ represents hydrogen and $R^1$ represents 1,2,2,2-tetrabromoethyl or 1,2-dibromo-2,2-dichloroethyl.

9. A compound according to claim 1 wherein $R^1$ represents a group of the formula:

           IV wherein $R^7$, $R^8$ and $R^9$ which may be the same or different, each is a $C_1$–$C_4$ alkyl group, a trifluoromethyl group or a halogeno group and wherein one or two of $R^7$, $R^8$ and $R^9$ may also represent hydrogen or a phenyl or substituted phenyl group.

10. A compound according to claim 9 wherein $R^9$ represents hydrogen and $R^7$ and $R^8$ each represent chlorine or each represent bromine.

11. A compound according to claim 1 wherein R represents

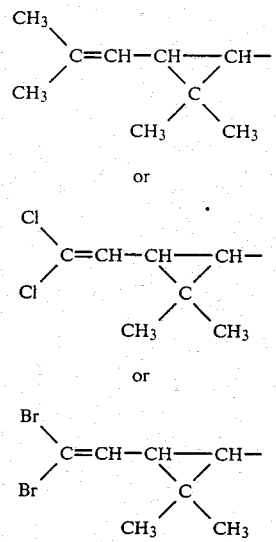

12. A compound according to claim 1 wherein $R^2$ represents hydrogen, the hydrogens at $C_1$ and $C_3$ of the cyclopropane ring are substantially completely in the cis or substantially completely in the trans configuration and $C_1$ on the cyclopropane ring has substantially completely R configuration.

13. A compound according to claim 1 wherein Ar is a benzene ring residue, $R^6$ represents at least one F, Cl, Br, $OCHF_2$ or $OCF_3$ group which may be the same or different, at least one $R^6$ being present in the para position on Ar, and $R^5$ is alkyl group containing a secondary carbon atom.

14. A compound according to claim 1 where R represents

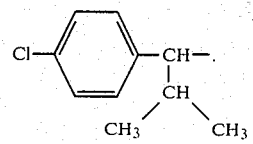

15. A compound according to claim 1 wherein D represents CN and the carbon atom to which the CN group is bonded has substantially completely R or substantially completely S configuration.

16. A compound according to claim 1 wherein the configuration at the double bond of the $-(CH_2)_bCH=NOR_a$ group is substantially completely E or substantially completely Z.

17. α-Cyano-3-methoximinomethylbenzyl-3-(2,2-dibromovinyl)-2,2-dimethylcyclopropane carboxylate.

18. A pesticidal composition comprising a compound according to claim 1 together with an inert carrier or diluent.

19. A composition according to claim 18 comprising a further pesticidal compound.

20. A method of controlling pest infestation which comprises applying to a pest or to a surface or an environment susceptible to pest infestation a compound according to claim 1 or composition according to claim 18.

21. A compound of the formula:

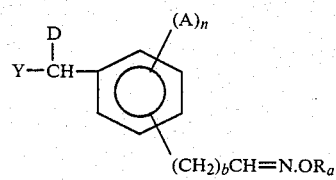           II where Y represents OH or a halogeno group and D, A, $R_a$, b and n are as defined in claim 1.

22. A compound of the formula:

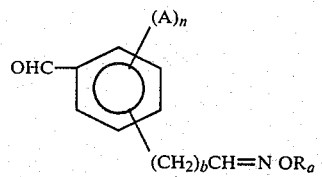           IIA wherein A, $R_a$, b and n are as defined in claim 1.

* * * * *